US009839653B2

(12) United States Patent
De Munter et al.

(10) Patent No.: US 9,839,653 B2
(45) Date of Patent: Dec. 12, 2017

(54) METHOD FOR REDUCING THE INFLAMMATORY ACTIVITY OF A STEM CELL TRANSPLANT AND USE THEREOF

(71) Applicant: Neuroplast Beheer B.V., Maastricht (NL)

(72) Inventors: Johannes Petrus Jozef Maria De Munter, Banholt (NL); Ekkehard Lang, Weinbach (DE); Erik Charles Marie Joseph Wolters, Amsterdam (NL); Petrus Theodorus De Haan, Oegstgeest (NL)

(73) Assignee: NEUROPLAST BEHEER B.V., Maastricht (NL)

( * ) Notice: Subject to any disclaimer, the term of this patent is extended or adjusted under 35 U.S.C. 154(b) by 0 days.

(21) Appl. No.: 15/029,206

(22) PCT Filed: Oct. 24, 2014

(86) PCT No.: PCT/EP2014/072911
§ 371 (c)(1),
(2) Date: Apr. 13, 2016

(87) PCT Pub. No.: WO2015/059300
PCT Pub. Date: Apr. 30, 2015

(65) Prior Publication Data
US 2016/0228468 A1 Aug. 11, 2016

(30) Foreign Application Priority Data

Oct. 24, 2013 (EP) .................... 13190120

(51) Int. Cl.
| *A61K 35/12* | (2015.01) |
| *A61K 35/28* | (2015.01) |
| *A01K 67/027* | (2006.01) |
| *A61K 35/16* | (2015.01) |
| *C12N 5/00* | (2006.01) |
| *C12N 5/0789* | (2010.01) |
| *C12N 5/0775* | (2010.01) |
| *A61K 38/17* | (2006.01) |

(52) U.S. Cl.
CPC .......... *A61K 35/28* (2013.01); *A01K 67/0271* (2013.01); *A61K 35/16* (2013.01); *A61K 38/1722* (2013.01); *C12N 5/0087* (2013.01); *C12N 5/0647* (2013.01); *C12N 5/0663* (2013.01); *A01K 2207/30* (2013.01); *A01K 2227/105* (2013.01); *A01K 2267/0356* (2013.01); *A01K 2267/0368* (2013.01); *A61K 2035/124* (2013.01); *C12N 2533/56* (2013.01)

(58) Field of Classification Search
CPC ............................................. A61K 2035/124
See application file for complete search history.

(56) References Cited

U.S. PATENT DOCUMENTS

| 5,087,570 A | 2/1992 | Weissman et al. |
| 5,137,809 A | 8/1992 | Loken et al. |
| 2002/0058289 A1 | 5/2002 | Thomas |
| 2004/0058397 A1 | 3/2004 | Thomas et al. |
| 2006/0246042 A1 | 11/2006 | Davies |
| 2009/0305406 A1 | 12/2009 | Pytlik et al. |
| 2012/0269774 A1 | 10/2012 | Ichim et al. |

FOREIGN PATENT DOCUMENTS

| GB | 2343679 A | 5/2000 |
| WO | 0029551 A1 | 5/2000 |
| WO | 02089726 A2 | 11/2002 |
| WO | 2007085210 A2 | 8/2007 |
| WO | 2008036374 A2 | 3/2008 |
| WO | 2015059300 A1 | 4/2015 |

OTHER PUBLICATIONS

Salahuddin et al., "Long-term suspension cultures of human cord blood myeloid cells," Blood 58(5):931-938, 1981.*
Cho et al., "High levels of B-cell activating factor during the peri-transplant period are associated with the reduced incidence of acute graft-versus-host disease following the myeloablative allogenic stem cell transplantation," Blood 114(22):878, 2009, meeting abstract.*
Dimitrios Davalos et al., "Fibrinogen as a key regulator of inflammation in disease", Seminars in Immunopathology, Springer, Berlin, DE., vol. 34, No. 1, Oct. 31, 2011 (Oct. 31, 2011), pp. 43-62.
R.A. Koll et al., "RheoSorb: A Specific Adsorber for Fibrinogen Elimination in Clinical Situations with Impaired Rheology," Artificial Organs, vol. 26. No. 2, Feb. 1, 2002 (Feb. 1, 2002), pp. 145-151.
Hirst C F et al., "Production of plasma selectively depleted in fibrinogen by affinity chromatography," Journal of Clinical Pathology, BMJ Publishing Group, GB, vol. 44, No. 4, Apr. 1, 1991 (Apr. 1, 1991), pp. 306-308.
De Munter et al., "Autologous stem cells in neurology: is there a future?" Journal of Neural Transmission, vol. 120, No. 1, Nov. 23, 2012 (Nov. 23, 2012), pp. 65-73.
Karina T. Wright et al., "Concise Review: Bone Marrow for the Treatment of Spinal Cord Injury: Mechanisms and Clinical Applications," Stem Cells, vol. 29, No. 2, Feb. 24, 2011 (Feb. 24, 2011), pp. 169-178.
Riordan Neil H et al., "Cord blood in regenerative medicine: do we need immune suppression?" Journal of Translational Medicine, Biomed Central, London, GB, vol. 5, No. 1, Jan. 30, 2007 (Jan. 30, 2007), p. 8.
Moviglia G A et al., 11 Autoreactive T cells induce in vitro BM mesenchymal stem cell transdifferentiation to neural stem cells, Cytotherapy, ISIS Medical Media, Oxford, GB, vol. 8, No. 3, May 1, 2006 (May 1, 2006), pp. 196-201.
PCT International Search Report and Written Opinion, PCT/EP2014/072911, dated Jan. 7, 2015.

\* cited by examiner

*Primary Examiner* — Rosanne Kosson
(74) *Attorney, Agent, or Firm* — TraskBritt, P.C.

(57) ABSTRACT

The disclosure is in the field of cell therapy, more in particular, stem cell transplantation therapy. The disclosure provides methods and compositions for improving the efficacy of stem cell transplantation therapy by reducing the inflammatory activity of a stem cell transplant. More in particular, the disclosure provides a method for preparing a stem cell transplant with reduced inflammatory activity comprising a step of suspending a composition comprising stem cells in a fibrinogen-depleted plasma and/or in a fibrinogen and C-reactive protein-depleted plasma.

7 Claims, No Drawings

METHOD FOR REDUCING THE INFLAMMATORY ACTIVITY OF A STEM CELL TRANSPLANT AND USE THEREOF

CROSS-REFERENCE TO RELATED APPLICATIONS

This application is a national phase entry under 35 U.S.C. §371 of International Patent Application PCT/EP2014/072911, filed Oct. 24, 2014, designating the United States of America and published in English as International Patent Publication WO 2015/059300 A1 on Apr. 30, 2015, which claims the benefit under Article 8 of the Patent Cooperation Treaty to European Patent Application Serial No. 13190120.9, filed Oct. 24, 2013.

TECHNICAL FIELD

The disclosure is in the field of cell therapy, more in particular, stem cell transplantation therapy. The disclosure provides methods and compositions for improving the efficacy of stem cell transplantation therapy by providing means and methods for reducing the inflammatory activity of a stem cell transplant. The disclosure also provides means and methods for obtaining a stem cell transplant with a reduced inflammatory activity.

BACKGROUND

The ability of tissues and organs to regenerate throughout life is the result of the presence of tissue-resident stem cells. During homeostasis, dying cells undergo programmed cell death or apoptosis and are replenished by cells descending from stem cells. Stem cell division results in a new stem cell and a cell that differentiates into a mature tissue cell when provided with the proper molecular signals.

After wounding or pathogen infection, however, cells in injured or infected tissue undergo necrosis and release danger-associated or pathogen-associated molecular patterns (DAMPs or PAMPs), respectively. These molecular patterns induce inflammatory processes at the site of injury or infection. During tissue inflammation, acute phase proteins are produced in the liver and are secreted in the blood plasma.

Acute phase proteins including fibrinogen and C-reactive protein activate the complement system, macrophages and cells of the adaptive immune system. Inflammation promotes hemostasis and recruits and activates cells of the innate and adaptive immune system, leading to blood coagulation and the removal of the injured or infected cells. After this, the inflammation stops, the homeostasis is restored and the damaged tissue is repaired by replenishment with stem cell descendants. In case the cell damage extends a certain limit or in case the infection becomes chronic, the plasma levels of acute phase proteins remain elevated and the inflammation becomes exacerbated, which results in excessive deposition of amyloids (plaque formation) and collagen (tissue scarification) leading to a significant loss-of-function of the affected tissue/organ.

Patients with certain cancers of the blood or bone marrow, such as multiple myeloma or leukemia, are treated by hematopoietic stem cell transplantations. In hematopoietic stem cell transplantations, the recipient's immune system is destroyed with radiation or chemotherapy before the transplantation with stem cell transplants from another (allogeneic) individual (the donor). Allogeneic hematopoietic stem cell transplantation to restore hematopoiesis in the recipient remains a dangerous procedure with the graft-versus-host disease as the major complication. Graft-versus-host disease is an inflammatory disease in which cells and components with a pro-inflammatory capability, such as cells of the immune system and acute phase proteins, present in the transplant, attack cells of the recipient. This can occur even if the donor and recipient carry identical major histocompatibility (MHC) proteins on their surface, because the immune system can still recognize other minor differences between cell surface proteins of the donor and recipient. In addition, the destruction of the recipients' immune system by radiation or chemotherapy prior to the stem cell transplantation results in the accumulation of large numbers of necrotic cells in the bone marrow, which enhances the graft-versus-host response.

Cell necrosis and inflammation is a major driver of tissue damage after insults of the central nervous system and in neurodegenerative diseases. Central nervous system injury including ischemic stroke, traumatic brain injury, and traumatic spinal cord injury represents a major burden to the healthcare system worldwide. Ischemic and traumatic insults of the central nervous system both result in definite chronic disability with an impaired life expectancy. Currently, post-traumatic defects of the central nervous system, such as spinal cord and/or brain injuries, cannot be treated, nor can the underlying histological defects be cured.

The majority of neurodegenerative diseases are sporadic conditions that are characterized by progressive loss of cells in the nervous system. Examples of neurodegenerative diseases are Parkinson disease, Alzheimer's dementia, Huntington's disease, amyotrophic lateral sclerosis and Multiple Sclerosis. The World Health Organization predicts that neurodegenerative disorders will take over cancer to become the second leading cause of death. The available treatments for neurodegenerative diseases aim at improvement of symptoms, pain relief, and increased mobility. However, thus far, the current therapeutics available to treat patients with neurodegenerative diseases, alleviate only the disease symptoms and delay the time to progression to disabling stages.

Stem cell transplantation therapies involving stem cells to restore neurogenesis and provide functional recovery, is an attractive approach to treat nervous system diseases and disorders. Stem cell transplantation therapies to restore vascularization is an attractive approach to treat ischemic diseases and disorders.

Stem cells obtained from embryos, e.g., embryonic stem cells, hold great potential for regenerative medicine (H. Hentze et al., *Trends in Biotechnology* 25:24-32, 2007), however, they have a number of disadvantages, including the possibility of transplant rejection due to their allogeneic offspring and the possible teratoma formation in case the cells are not securely and quantitatively differentiated prior to transplantation.

Embryonic stem cells need to be cultured and consequently bear the risk of being exposed to xenogenic material or being contaminated with prematurely exhausted cells (F. Mannello and G. A. Tonti, *Stem Cells* 25:1603-1609, 2007). Due to the limited insight in the biology of embryonic stem cells and their developmental behavior, they currently do not appear to be safe enough for human application.

For the treatment of cancers of the blood or bone marrow, transplantation of allogeneic stem cells derived from the bone marrow or peripheral blood is the most efficient. For the treatment of diseases and disorders of the central nervous system, transplantation of autologous adult stem cells, mainly hematopoietic stem cells and mesenchymal stem cells derived from the bone marrow or peripheral blood, is considered to be the most promising (E. Sykova et al., *Cell Transplant* 15:675-687, 2006).

The bone marrow stroma harbors heterogeneous populations of multi-potent cells, including hematopoietic stem cells and mesenchymal stem cells capable of self-renewal and differentiation into various cells and tissues of, respectively, the hematopoietic and mesenchymal lineages.

Recent preclinical work investigating the feasibility of stem cell transplantation therapies to treat patients with ischemic stroke, traumatic brain injury, and traumatic spinal cord injury has shown that when applied intrathecally, hematopoietic stem cells and/or mesenchymal stem cells, or descendants thereof, are suggested to infiltrate into the lesioned neural tissue, penetrate glial scar tissue (M. R. Alison, *Journal of Pathology* 217:141-143, 2009), secrete trophic factors (A. I. Caplan and J. E. Dennis, *Journal of Cellular Biochemistry* 98:1076-1084, 2006), are capable of differentiation into functional neurons (R. Zeng et al., *Spine* 36:997-1005, 2011), promote the formation of synaptic connections (F. M. Bareyre, *Journal of Neurological Sciences* 265:63-72, 2008), and, as a result, participate in the reorganization of the neural network leading to a functional improvement (B. K. Kwon et al., *Experimental Neurology* 248C:30-44, 2013).

In early stem cell transplantation studies, bone marrow transplants were used, which were manufactured by single or double centrifugation of bone marrow biopsies (WO2007125420). The layer between the erythrocytes and the plasma named the buffy coat was subsequently collected. The buffy coat contains a heterogeneous population of nucleated cells. A significant portion of the nucleated cells are immunity-associated cells with a pro-inflammatory capability and allogeneic transplantation of these cells to restore hematogenesis frequently results in the graft-versus-host disease as stated above. Autologous transplantation of these cells into damaged central nervous system tissue may also lead to adverse or even detrimental effects toward the intended mode of action (K. L. Le Blanc et al., *Scandinavian Journal of Immunology* 57:11-20, 2003; G. M. Spaggiari et al., *Blood* 107:1484-1490, 2006; R. A. Adams et al., *Journal of Experimental Medicine* 204:571-582, 2007; B. Assmus et al., *Journal of the American College of Cardiology* 55:1385-1394, 2010; and K. D. Beck et al., *Brain* 133:433-447, 2010). In addition, the chemicals used during the gradient centrifugation step have to be removed from the transplants by introducing additional washing steps to obtain the final transplant product.

Separation of stem cells and progenitor cells from other cell types in tissue biopsies on the basis of their physical characteristics, such as density and sedimentation speed, technically, is very difficult. The limitations of separating stem cells and progenitor cells from other cell types were overcome by the application of monoclonal antibodies that specifically bind to cell surface proteins such as the cluster of differentiation (CD) proteins. Immune adsorption and flow cytometry techniques using the monoclonal antibodies labeled with magnetic beads or fluorescent molecules are currently employed to both positively and negatively select specific cell types out of heterogeneous cell populations.

In positive selection techniques, labeled antibodies are used to specifically bind the desired cells in the biopsy. The unwanted cells remain unlabeled and are removed. After the selection process, the desired cells have to be detached from the antibodies with a suitable solvent. As a consequence, the stem cells in the transplants are exposed to a medium that may negatively influence cell differentiation and, thus, the transplantation efficacy.

Currently, the majority of stem cell transplants used in animal and human studies aimed at improving neural and vascular tissues have been produced by positive selection of cells carrying specific surface proteins, followed by culturing of the selected cells to increase their numbers. It has, however, never been proven that the positively selected cells indeed have the capacity to differentiate into functional neurons and that they secrete the trophic factors required for full restoration of the neural system.

Generally, the results of intrathecal or intracerebral stem cell transplantations using stem cell transplants obtained by positive selection fluctuate and the beneficial effects are limited. This is most likely due to the fact that it is not known whether the desired beneficial stem cell types are present in the transplant preparations, or that the desired stem cell types lost their therapeutic capability during the timely stem cell processing/culturing process that generally exceeds 72 hours after collection of the bone marrow biopsies.

In negative cell selection, labeled antibodies are used to specifically bind the unwanted cells in the biopsy. The desired cells remain unlabeled and are collected.

Moviglia and coworkers (G. A. Moviglia et al., *Cytotherapy* 8:196-201, 2006) suggested a cocktail of anti-CD3, anti-CD4, anti-CD19, anti-CD38, anti-CD66b and anti-glycophorin A antibodies to selectively enrich for mesenchymal stem cells as well as anti-CD14, anti-CD16, anti-CD19, anti-CD56 and anti-glycophorin A to enrich CD3-positive cells by immune-rosetting for in vitro experiments.

Patent application U.S. 2002/058289 describes the treatment of bone marrow-derived cell suspensions with a range of antibodies specific for CD2, CD3, CD4, CD5, CD8, CD11b, CD15, CD16, CD19, CD20, CD21, CD22, CD24, CD33, CD38, CD56, CD66b and Glycophorin A to specifically enrich bone marrow biopsies for mesenchymal progenitors.

Patent application WO 02/089726 describes a method for making a homogeneous preparation of hematopoietic stem cells using a combination of cross-flow elutriation and labeling of unwanted cells with magnetically labeled antibodies. The method uses culturing of the resulting enriched cell populations and cell membrane dyes to verify cell identity, which makes the method impractical for therapeutic applications.

U.S. Pat. No. 5,087,570 describes a method for preparing a hematopoietic cell composition using a combination of positive and negative cell selection. The process relies on the use of an antibody to the Sca-1 antigen, which is associated with murine clonogenic bone marrow precursors of thymocytes and progeny T-cells. The Sca-1 antibody is not useful for isolating human hematopoietic cells.

U.S. Pat. No. 5,137,809 describes a method and kit for identifying and analyzing lineages and maturational stages of hematopoietic cells. The method uses a first monoclonal antibody (CD45) labeled with a fluorochrome to react with all leukocytes in a sample, followed by secondary monoclonal antibodies (CD15, CD16, CD10, CD34, CD20, CD19, CD14, CD3, CD11b) labeled with a second fluorochrome to react with a subpopulation of leukocytes. Cell selection is based on flow cytometry.

Stem cell transplants based on negative cell selection, in which cell types of the innate and adaptive immune system (macrophages, lymphocytes, granulocytes and the like) and erythroid cells (erythroblasts, erythrocytes) are removed, have been used in animal and human autologous transplantation studies. The studies using the transplants demonstrated that the beneficial efficacy still remained limited, preventing further clinical application.

Using a mouse model of spinal cord injury, it was confirmed that the stem cell transplants in which the cell types of the immune system and the erythroid cells were removed by negative cell selection have a limited efficacy when transplanted intrathecally.

This is due to the presence of cell types or components with a pro-inflammatory capability in the stem cell transplants, resulting in a negative effect on their therapeutic efficacy.

For these reasons, there is an unmet need for stem cell transplants that lack the pro-inflammatory capability when transplanted to an allogeneic or autologous recipient and that, as a result, will improve the efficacy of stem cell transplantation therapies.

BRIEF SUMMARY

The above objects have been met by this disclosure in that a method is provided for producing a stem cell transplant, for example, from a tissue sample such as a biopsy, with a reduced inflammatory activity. This method comprises a step of suspending stem cells in plasma that is depleted of pro-inflammatory proteins such as fibrinogen and C-reactive protein.

In a more preferred embodiment, the method provides an additional step of removing pro-inflammatory cells from the stem cell transplant. The stem cells are preferably obtained from bone marrow, peripheral blood and/or umbilical cord blood.

In another embodiment, the disclosure relates to a stem cell composition for use as a transplant with a reduced inflammatory activity in which pro-inflammatory proteins are removed. In a more preferred embodiment, the disclosure relates to a stem cell composition for use as a transplant in which the cells with a pro-inflammatory capability are also removed. The stem cell composition of the disclosure is suitable for neuronal and vascular tissue regeneration and for restoring hematogenesis.

The disclosure further relates to a method for restoring or improving neuronal, vascular and hematopoietic tissue in a subject by treating the subject with a transplant comprising a stem cell composition of the disclosure. In such a method, the stem cell transplant is either an autologous or an allogeneic transplant.

The disclosure therewith provides methods and compositions for improving the efficacy of stem cell transplantation therapy by reducing the inflammatory activity of a transplant comprising a stem cell composition. More in particular, the disclosure provides a method for preparing a stem cell transplant with reduced inflammatory activity comprising a step of suspending a composition comprising stem cells in a fibrinogen-depleted plasma and/or in a fibrinogen and C-reactive protein-depleted plasma.

DETAILED DESCRIPTION

Using animal models of spinal cord injury, it was surprisingly found that certain proteins present in the plasma of bone marrow have a negative effect on the efficacy of the stem cells obtained from the bone marrow, in particular, when they are used as a stem cell transplant and transplanted intrathecally to the autologous animal.

This negative effect appeared to be caused by the presence of the acute phase proteins fibrinogen and C-reactive protein in the bone marrow plasma. Removal of the two proteins by filtration optionally followed by removal of the cells with a pro-inflammatory capability, resulted in stem cell transplants with a significant improvement of the transplantation efficacy, compared with the effect obtained when a stem cell transplant was used wherein only the cells with a pro-inflammatory capability were removed.

It was concluded from this surprising result that the use of stem cell transplants in which the pro-inflammatory cells (such as macrophages, dendritic cells, lymphocytes and granulocytes) and acute phase proteins (such as fibrinogen and C-reactive protein) were removed, are superior in terms of transplantation efficacy compared to stem cell transplants of the prior art.

In a preferred embodiment, the disclosure, therefore, relates to a method for improving the efficacy of a stem cell transplant, wherein the stem cell transplant is depleted of fibrinogen and C-reactive protein. Optionally, the transplant is also depleted of pro-inflammatory cells.

The term "improved efficacy of a transplant" refers to the capability of a transplant, in particular, a stem cell transplant, to repair damaged tissue, in particular, neuronal tissue.

As used herein, the term "stem cell transplant" refers to a composition comprising stem cells, wherein the composition is suitable for administration by transplantation into a subject.

The stem cell transplant of the disclosure may advantageously be obtained from a tissue biopsy, such as peripheral blood, umbilical cord blood or bone marrow. Collection of bone marrow or peripheral blood for use in autologous or allogeneic stem cell transplantation therapies is common practice, and methods to collect bone marrow or peripheral blood biopsies are well known in the art.

The term "intrathecal" as used herein is an adjective that refers to something introduced into or occurring in the space under the arachnoid membrane of the brain or spinal cord.

The term "pro-inflammatory capability" or the like is the capacity of cells or other components to initiate the process of inflammation in vivo, characterized by the accumulation of pro-inflammatory cytokines. The skilled person is well aware of options to determine the pro-inflammatory capacity of a compound.

As used herein, the term "reduced inflammatory activity" is to be interpreted as the inflammatory activity of a composition in comparison to a reference composition. A suitable reference composition in respect of a preferred embodiment of the disclosure (i.e., a composition comprising a stem cell in a plasma depleted of fibrinogen and/or C-reactive protein) would be a composition comprising stem cells resuspended in a normal plasma or a plasma not depleted of fibrinogen and/or C-reactive protein.

The term "plasma" is used herein to refer to the pale-yellow liquid component of blood that normally holds the blood cells in whole blood in suspension. It makes up about 55% of the body's total blood volume. It is the intravascular fluid part of extracellular fluid (all body fluid outside of cells). It consists of mostly water (up to 95% by volume), and contains dissolved proteins (6-8%) (i.e., serum albumins, globulins, and fibrinogen), glucose, clotting factors, electrolytes ($Na^+$, $Ca^{2+}$, $Mg^{2+}$, $HCO_3^-$, $Cl^-$, etc.), hormones, and carbon dioxide (plasma being the main medium for excretory product transportation). Serum is blood plasma without clotting factors. The terms "serum" and "plasma" are used interchangeably herein, i.e., where it reads "serum," it also refers to "plasma," and vice versa.

The inflammatory activity of a composition may be determined by routine assays available to the skilled person, such as immunological and histochemical methods. Inflammatory activity may also be measured by immunochemical methods in samples taken from the transplantation site, wherein the presence of inflammatory markers such as the cytokines interleukin 1 and interferon gamma is assessed.

In a preferred embodiment, the composition according to the disclosure has an inflammatory activity that is less than the inflammatory activity of a composition comprising the same cells in a plasma or serum that is not depleted of fibrinogen and/or C-reactive protein. "Less" in this respect, means at least 10% less, such as 20%, 30% or 50% less. Preferably, the inflammatory activity of a composition according to the disclosure is less than 40% of the reference composition, such as 30%, 20% or 10% or less. Most preferred is an inflammatory activity close to zero or not detectable.

This disclosure, therefore, also relates to a method for reducing the inflammatory activity of a stem cell transplant comprising a step of removing fibrinogen and C-reactive protein from the transplant. A composition comprising stem cells for use as a transplant may also be obtained by resuspending stem cells in serum or plasma depleted of fibrinogen and/or C-reactive protein.

Such may effectively be accomplished by using a step of filtration. Hence, the disclosure relates to a method as described above wherein the fibrinogen and C-reactive protein are removed by filtration. In another embodiment, the fibrinogen and C-reactive protein may be removed by density-gradient centrifugation. In yet another embodiment, the fibrinogen and C-reactive protein may be removed by chromatography.

The method according to the disclosure is particularly useful when the stem cell transplant is also depleted of pro-inflammatory cells. The disclosure, therefore, also relates to a method as described above, additionally comprising a step of removing cells with a pro-inflammatory capability, such as the macrophages, dendritic cells, lymphocytes and granulocytes.

The cells may be removed by negative cell selection or any other method known in the art per se. The different steps of the method may be conducted in a random order.

Negative cell selection may involve a step of reacting a stem cell transplant containing multiple cell lineages with an antibody composition containing antibodies specifically binding to the antigens CD235a (glycophorin A), CD2 and/or CD3, CD14 and/or CD16 and CD19 and/or CD 20 for selective depletion of the target cell erythrocytes, lymphocytes, macrophages, dendritic cells and granulocytes. The antibody composition added includes the suspension medium of the antibodies, mainly consisting of a buffered saline solution for each antibody.

The antibodies in the antibody composition may be magnetically labeled, so that the target cells present in the stem cell transplant can be selectively labeled and removed by retention upon the application of magnetic force to the sample.

A method is herein provided for the selective depletion of cell lineages defined by antibody-mediated recognition of specific epitopes, preferably, but not limited to, erythrocytes, lymphocytes, macrophages, dendritic cells and granulocytes from stem cell transplants obtained from the human body, preferably, but not limited to, human bone marrow.

In a more preferred embodiment, a stem cell transplant is reacted with an antibody composition containing antibodies capable of binding to the antigens CD3, CD14, CD19 and CD235a. The antibodies may be magnetically labeled, so that target cells can selectively labeled and removed by retention upon the application of magnetic force to the sample.

In a preferred embodiment of a method according to the disclosure, unwanted cell populations are removed from a full volume of a stem cell transplant by the application of specific magnetically labeled antibodies. In an even more preferred embodiment, those antibodies comprise, but are not limited to, antibodies specific for CD2 and/or CD3 to remove T-lymphocytes, antibodies specific for CD19 and/or CD20 to remove B-lymphocytes, CD14 and/or CD 16 for removal of granulocytes, monocytes, dendritic cells and macrophages. In another embodiment, antibodies are specific for CD235a and/or Glycophorin A to remove erythrocytes.

The disclosure also relates to a stem cell transplant obtained in a method as described above. These methods yield a stem cell transplant in which fibrinogen and C-reactive protein are removed. The disclosure, in particular, relates to a stem cell transplant as described above, in which cells with a pro-inflammatory capability are removed.

The terms "removal," "depletion," "removed," "depleted," or the like, refer to a reduction in the protein amount or cell number in the stem cell transplant of the disclosure of at least 90 percent or 99 percent, compared to the protein amount or cell number in the tissue biopsy such as the bone marrow. The fibrinogen concentration in the blood plasma ranges between 1.5 to 4 grams per liter. In a preferred embodiment, the transplants of the disclosure contain less than 0.4 grams of fibrinogen per liter. In a more preferred embodiment, a plasma preparation suitable for use in a method according to the disclosure, contains less than 40 milligrams of fibrinogen per liter, such as less than 4 milligrams per liter. In a further preferred embodiment, a composition comprising stem cells for use according to the disclosure comprises less than 0.4 gram of fibrinogen per liter, such as less than 40 milligrams or less than 4 milligrams per liter.

The C-reactive protein concentration in blood plasma varies considerably among individuals, but generally ranges between 10 to 100 milligrams per liter. In a preferred embodiment, the transplants of the disclosure contain less than 10 milligrams of C-reactive protein per liter. In a more preferred embodiment, the transplants of the disclosure contain less than 1 milligram of C-reactive protein per liter.

The lymphocyte number in the blood plasma ranges between 1 to 4 thousand per microliter. In a preferred embodiment, the transplants of the disclosure contain less than 400 lymphocytes per microliter. In a more preferred embodiment, the transplants of the disclosure contain less than 40 lymphocytes per microliter. The granulocyte number in the blood plasma ranges between 2.5 to 7.5 thousand per microliter. In a preferred embodiment, the transplants of the disclosure contain less than 750 granulocytes per microliter. In a more preferred embodiment, the transplants of the disclosure contain less than 75 granulocytes per microliter. The dendritic cell and macrophage number in the blood plasma ranges between 10 to 800 per microliter. In a preferred embodiment, the final transplants of the disclosure contain less than 80 dendritic cells or macrophages per microliter. In a more preferred embodiment, the transplants of the disclosure contain less than 8 dendritic cells or macrophages per microliter.

In a preferred embodiment, the disclosure relates to a method as described above, wherein the stem cell transplant is suitable for hematopoietic tissue regeneration. Such a stem cell transplant is particularly suited for restoring hematogenesis. Hence, the disclosure also provides a method for restoring hematogenesis in a subject with a stem cell transplant as described herein.

In another preferred embodiment, the disclosure relates to a method as described above, wherein the stem cell transplant is suitable for vascular tissue regeneration. Such a stem cell transplant is particularly suited for restoring vascularization. Hence, the disclosure also provides a method for restoring vascularization in a subject with a stem cell transplant as described herein.

In a particularly preferred embodiment, the disclosure relates to a method as described above, wherein the stem cell transplant is suitable for neural tissue regeneration. Such a stem cell transplant is particularly suited for neurogenesis. Hence, the disclosure also provides a method for restoring or improving neurogenesis in a subject by treating the subject with a stem cell transplant as described herein.

Recipients of the stem cell transplants of the disclosure can be autologous or allogeneic. In a preferred embodiment, the stem cell transplant of the disclosure is an autologous transplant. In another embodiment, the stem cell transplant of the disclosure is an allogeneic transplant.

This disclosure broadly contemplates a process for enriching and recovering human stem and progenitor cells for the therapeutic treatment of different indications, preferably by tailoring a composition suitable for injection, comprising a cell composition derived from blood, umbilical cord blood or bone marrow. The skilled person is well aware of the metes and bounds of such a composition or method regarding product volume and qualitative and quantitative cell content.

EXAMPLES

Example 1: Preparation of a Human Stem Cell Transplant

Bone marrow was collected from a healthy volunteer by aspiration using a syringe with a five-hole bone marrow needle with two bone punctures. The needle was repositioned after every filled syringe. In total, a biopsy of 50 ml of bone marrow was obtained. The biopsy was centrifugated in a SEPAX® II cell separator (Biosafe) using a low centrifugal force (slow speed) according to the recommendations of the manufacturer. In that way, three fractions were obtained. First, the plasma fraction, containing all soluble proteins of the biopsy. Second, a fraction containing the erythrocytes and thrombocytes was obtained. The third fraction was a composition comprising the nucleated bone marrow cells (also often referred to as the "buffy coat"), including the hematopoietic and mesenchymal stem cells. This is hereinafter referred to as "stem cell composition A."

The plasma fraction was depleted of fibrinogen and C-reactive protein by filtration using a THERASORB® Fibrinogen-specific filter (Miltenyi). The resulting plasma, from which the fibrinogen and C-reactive protein was removed, was subsequently used to resuspend the nucleated bone marrow cells from the third fraction (stem cell composition A) in a Cell Preparation Bag (Miltenyi). In that way, a stem cell composition was obtained that is herein further referred to as "stem cell composition B."

The stem cell composition B was contacted with magnetically labeled antibodies against CD3, CD14, CD19 and CD235a (Miltenyi). The bag was subsequently connected to a magnetic cell separation device (CLINIMACS® PLUS System, Miltenyi) in order to produce a stem cell composition depleted of erythrocytes, thrombocytes, lymphocytes, granulocytes, dendritic cells, macrophages, fibrinogen and C-reactive protein. This stem cell composition is hereinafter referred to as "stem cell composition C."

Stem cell composition D consisted of stem cell preparation A resuspended in the plasma fraction from the same subject, not depleted of fibrinogen and C-reactive protein. This composition acted as a reference composition.

Example 2: Allogeneic Transplantation Experiment

An experimental animal model was used for spinal cord injury to compare the efficacy of the various compositions comprising stem cells. The animal model was a T-lymphocyte-deficient rat. Traumatic compression lesions of the spinal cord were induced by balloon dilation. Three days thereafter, the stem cell compositions were administered intrathecally in close proximity of the spinal cord lesion in the animal. The animals were monitored for thirty-five days. In this period, the body weight was measured and the animals underwent the catwalk and rotarod (Panlab) tests as measures of the neurological damage. After 35 days, the animals were sacrificed and the spinal cord lesions were examined histologically.

In this experimental set-up, animals received stem cell transplants comprising stem cell compositions A, B, C and D, with normal plasma and untreated animals as a control. It was scored how the four compositions were able to repair the neurological damage after induction of traumatic spinal cord lesions.

After 35 days, it was observed that the degree of neurological improvement of the lesioned animals treated with a stem cell transplant according to the disclosure (stem cell compositions B and C) was significantly higher than that of the untreated animals or those treated with plasma, or stem cell compositions A and D. Furthermore, the neurological improvement of the animals treated with stem cell composition C was significantly higher than that of animals treated with stem cell composition B.

TABLE 1

| Experimental condition | Stem Cell Composition(*) | | | | Negative Control (plasma) | Negative Control (lesioned rat) | Positive Control (normal rat) |
| --- | --- | --- | --- | --- | --- | --- | --- |
| | A | B | C | D | | | |
| Catwalk | +/− | + | ++ | +/− | − | − | +++ |
| Rotarod | +/− | + | ++ | +/− | − | − | +++ |
| Body weight | +/− | + | ++ | +/− | − | − | +++ |
| Histological findings | +/− | + | ++ | +/− | − | − | +++ |

The performance or condition of the lesioned rats has been put on 0 percent (baseline) and the normal rats on 100 percent.

−=equal or worsening of the performance or condition (−15 to 5 percent compared to baseline).

+/−=about the same or slightly better performance or condition (between −15% to 10% compared to baseline)

+=slight improvement of the performance or condition (5 to 10 percent compared to baseline)

++=large improvement of the performance or condition (10 to 40 percent compared to baseline)

+++=Normal performance or condition of untreated rats (90 to 100 percent compared to baseline)

Example 3: Preparation of a Rat Stem Cell Transplant

Stem cell compositions E, F, G and H were prepared from normal Wistar rats in an analogous way as described in Example 1 for their human equivalents. Sample E contained the nucleated bone marrow cells without plasma; sample F were the nucleated bone marrow cells in plasma depleted of fibrinogen and C-reactive protein; and sample G is composition F additionally depleted of erythrocytes, thrombocytes, lymphocytes, granulocytes, dendritic cells and macrophages. Sample H is a control sample corresponding to human sample D wherein the cells from sample E were resuspended in normal rat plasma comprising fibrinogen and C-reactive protein.

Example 4: Autologous Transplantation Experiment

Essentially, the same experimental set-up was used as described in Example 2 to compare the efficacy of the various compositions comprising rat stem cells obtained in Example 3. The animal model was a normal immunocompetent Wistar rat. Traumatic compression lesions of the spinal cord were induced by balloon dilation. Three days thereafter, the stem cell compositions were administered intrathecally in close proximity to the spinal cord lesion in the animal. The animals were monitored for thirty-five days. In this period, the body weight was measured and the animals underwent the catwalk and rotarod (Panlab) tests as measures of the neurological damage. After 35 days, the animals were sacrificed and the spinal cord lesions were examined histologically.

In this experimental set-up, animals received stem cell transplants comprising stem cell compositions E, F, G and H with normal plasma and untreated animals as a control. It was scored how the four compositions were able to repair the neurological damage after induction of traumatic spinal cord lesions.

After 35 days, it was observed that the degree of neurological improvement of the lesioned animals treated with a stem cell transplant according to the disclosure (stem cell compositions F and G) was significantly higher than that of the untreated animals or those treated with plasma, or stem cell compositions E and H. Furthermore, the neurological improvement of the animals treated with stem cell composition G was significantly higher than that of animals treated with stem cell composition F.

Three days after transplant, intrathecal fluid from the lesion site was obtained and tested for the presence of an inflammatory marker, e.g., interferon gamma using a rat IFN gamma ELISA kit (Pierce protein biology products). It was found that interferon gamma levels were high in the intrathecal fluid from animals receiving stem cell compositions E and H. The interferon gamma levels in the intrathecal fluid from animals receiving stem cell compositions F and G were considerably less, 30% and 10%, respectively, of the level in animals receiving stem cell composition H.

TABLE 1 (CONTINUED)

| Experimental condition | Stem Cell Composition(*) | | | | Negative Control (plasma) | Negative Control (lesioned rat) | Positive Control (normal rat) |
| --- | --- | --- | --- | --- | --- | --- | --- |
| | E | F | G | H | | | |
| Catwalk | +/− | + | ++ | +/− | − | − | +++ |
| Rotarod | +/− | + | ++ | +/− | − | − | +++ |
| Body weight | +/− | + | ++ | +/− | − | − | +++ |
| Histological findings | +/− | + | ++ | +/− | − | − | +++ |

The performance or condition of the lesioned rats has been put on 0 percent (baseline) and the normal rats on 100 percent.

−=equal or worsening of the performance or condition (−15 to 5 percent compared to baseline).

+/−=about the same or slightly better performance or condition (between −15% to 10% compared to baseline)

+=slight improvement of the performance or condition (5 to 10 percent compared to baseline)

++=large improvement of the performance or condition (10 to 40 percent compared to baseline)

+++=Normal performance or condition of untreated rats (90 to 100 percent compared to baseline)

The invention claimed is:

1. An in vitro method for producing a hematopoietic stem cell composition with reduced inflammatory activity, the method comprising:
   suspending a composition comprising nucleated cells comprising at least one stem cell in plasma or serum depleted of fibrinogen and C-reactive protein,
   thereby obtaining a stem cell composition with reduced inflammatory activity.

2. The method according to claim 1, wherein the composition comprising nucleated cells is obtained from a tissue sample taken from a subject.

3. The method according to claim 2, wherein the subject is a human subject.

4. The method according to claim 2, wherein the plasma or serum depleted of fibrinogen and C-reactive protein is obtained from the same subject as the subject from which the tissue sample is obtained.

5. The method according to claim 1, additionally comprising a step of depleting pro-inflammatory cells from the composition comprising nucleated cells.

6. The method according to claim 1, wherein the fibrinogen and C-reactive protein depleted plasma or serum is obtained by filtration and/or chromatography.

7. The method according to claim 2, wherein the tissue is selected from the group consisting of bone marrow, peripheral blood and umbilical cord blood.

* * * * *

UNITED STATES PATENT AND TRADEMARK OFFICE
CERTIFICATE OF CORRECTION

PATENT NO.       : 9,839,653 B2
APPLICATION NO.  : 15/029206
DATED            : December 12, 2017
INVENTOR(S)      : Johannes Petrus Jozef Maria De Munter et al.

Page 1 of 1

It is certified that error appears in the above-identified patent and that said Letters Patent is hereby corrected as shown below:

In the Specification

Column 8,  Line 8,  change "and/or CD 16 for" to --and/or CD16 for--

In the Claims

Claim 7,  Column 12,  Line 50,  change "of hone marrow," to --of bone marrow,--

Signed and Sealed this
Eighth Day of May, 2018

Andrei Iancu
*Director of the United States Patent and Trademark Office*